United States Patent [19]

Jevne et al.

[11] Patent Number: 5,525,356
[45] Date of Patent: Jun. 11, 1996

[54] AMPHOTERIC N-SUBSTITUTED ACRYLAMIDE HYDROGEL AND METHOD

[75] Inventors: Allan H. Jevne, Anoka; Carolann Holmblad, Cambridge; Joseph B. Phipps, Plymouth; Warren W. Howland, Champlin, all of Minn.

[73] Assignee: Medtronic, Inc., Minneapolis, Minn.

[21] Appl. No.: 776,251

[22] PCT Filed: Mar. 29, 1991

[86] PCT No.: PCT/US91/02156

§ 371 Date: Nov. 14, 1991

§ 102(e) Date: Nov. 14, 1991

[87] PCT Pub. No.: WO91/15250

PCT Pub. Date: Oct. 17, 1991

Related U.S. Application Data

[63] Continuation-in-part of Ser. No. 502,841, Mar. 30, 1990, abandoned.

[51] Int. Cl.$^6$ ...................................................... A61K 9/10
[52] U.S. Cl. ........................... 424/484; 424/486; 514/944
[58] Field of Search .................................. 424/484, 486; 514/944

[56] References Cited

U.S. PATENT DOCUMENTS

| | | | |
|---|---|---|---|
| 3,428,043 | 2/1969 | Shepherd et al. | 128/156 |
| 3,783,869 | 1/1974 | Schnipper | 128/261 |
| 4,078,568 | 3/1978 | Etes et al. | 128/283 |
| 4,153,055 | 5/1979 | Etes | 128/156 |
| 4,226,232 | 10/1980 | Spence | 128/156 |
| 4,384,898 | 5/1983 | Okada et al. | 127/40 |
| 4,391,278 | 7/1983 | Cahalan et al. | 128/640 |
| 4,391,799 | 7/1983 | Mason, Jr. et al. | 424/132 |
| 4,393,048 | 7/1983 | Mason, Jr. et al. | 424/132 |
| 4,486,193 | 12/1984 | Shaw et al. | 604/897 |
| 4,552,138 | 11/1985 | Hofeditz et al. | 128/156 |
| 4,556,056 | 12/1985 | Fischer | 128/156 |
| 4,570,629 | 2/1986 | Widra | 128/156 |
| 4,581,821 | 4/1986 | Cahalan et al. | 29/877 |
| 4,593,053 | 6/1986 | Jevne et al. | 523/111 |
| 4,650,484 | 3/1987 | Shaw et al. | 604/897 |
| 4,659,572 | 4/1987 | Murray | 424/448 |
| 4,699,146 | 10/1987 | Sieverding | 128/640 |
| 4,704,119 | 11/1987 | Shaw et al. | 604/897 |
| 4,706,680 | 11/1987 | Keusch et al. | 128/640 |
| 4,725,272 | 2/1988 | Gale | 424/448 |
| 4,750,482 | 6/1988 | Sieverding | 128/156 |

(List continued on next page.)

FOREIGN PATENT DOCUMENTS

| | | |
|---|---|---|
| 0355536 | 2/1990 | European Pat. Off. . |
| 61-23670 | 1/1986 | Japan . |
| 63-130529 | 6/1988 | Japan . |

OTHER PUBLICATIONS

Biological Tolerance of Poly(N–Substituted Acrylamides); J. Kopecek, L. Sprincl, H. Bazilova and J. Vacik; Institute of Macromolecular Chemistry, Czechoslovak Academy of Sciences, Prague; J. Biomed Mater, Res.; vol. 7, pp. 111–121 (1973).

Polymerization of Vinylpyridinium Salts, IX., Preparation of Monomeric Salt Pairs; Polymer Letters Edition, vol. 15, pp. 487–491 (1977).

*Primary Examiner*—Raj Bawa
*Attorney, Agent, or Firm*—Daniel W. Latham; Harold R. Patton

[57] ABSTRACT

A polymeric, amphoteric hydrogel for use in medical devices and medical devices using the hydrogel. The hydrogel has a first polymer repeating unit having a acid group and a second polymer repeating unit having a base group such that the acid groups and base groups are present in the hydrogel in amounts effective to provide a hydrogel with a strong, amphoteric, nonmobile ionic structure. For example, the hydrogel can be a copolymer of 2-acrylamido-2-methylpropane sulfonic acid and methacrylamido-propyl-trimethylammonium hydroxide. The hydrogel can be an adhesive used to adhere medical devices to the skin of a patient. It can be particularly useful in drug delivery applications such as in iontophoresis devices.

21 Claims, 1 Drawing Sheet

U.S. PATENT DOCUMENTS

| | | | |
|---|---|---|---|
| 4,767,619 | 8/1988 | Murray | 424/78 |
| 4,768,523 | 9/1988 | Cahalan et al. | 128/785 |
| 4,777,954 | 10/1988 | Keusch et al. | 128/640 |
| 4,781,921 | 11/1988 | Smith et al. | 424/81 |
| 4,820,263 | 4/1989 | Spevak et al. | 604/20 |
| 4,830,776 | 5/1989 | Thompson | 252/500 |
| 4,842,597 | 6/1989 | Brook et al. | 604/368 |
| 4,846,826 | 7/1989 | Shaw et al. | 604/890.1 |
| 4,867,821 | 9/1989 | Morgan et al. | 156/152 |
| 4,889,530 | 12/1989 | Smith et al. | 604/304 |
| 4,904,247 | 2/1990 | Therriault et al. | 604/304 |
| 4,909,244 | 3/1990 | Quarfoot et al. | 128/156 |
| 4,920,158 | 4/1990 | Murray et al. | 523/111 |
| 4,930,500 | 6/1990 | Morgan | 128/156 |

AMPHOTERIC N-SUBSTITUTED ACRYLAMIDE HYDROGEL AND METHOD

This is a continuation-in-part of copending application Ser. No. 07/502,841 filed on Mar. 30, 1990 now abandoned.

FIELD OF THE INVENTION

This invention relates to polymeric hydrogels for use on medical devices such as iontophoresis, sensing electrodes stimulation electrodes, wound dressings, passive drug delivery devices and the like to adhere the device to the patient's skin. The invention also relates to hydrogels for implantable drug delivery reservoirs, cushions for implantable devices such as heart pacemakers, defibrilators, leads, catheters, and the like.

BACKGROUND OF THE INVENTION

Polymeric, conductive hydrogels have been used in medical devices to adhere the device to a patient's skin, such as biomedical electrodes to provide a secure, conductive connection between the medical device and the patient's skin for stimulation or sensing purposes. However, in certain applications such as iontophoresis devices, known hydrogel compositions possess significant disadvantages.

Iontophoresis is a method for introducing active pharmaceutical agents into a patient. The method utilizes electrical current to transport the active agents, which are usually in charged form, but may also be uncharged, through the skin, mucosa or other body surface of the patient. The iontophoresis process has been found to be useful in the administration of lidocaine hydrochloride, hydrocortisone derivatives, penicillin, dexamethasone sodium phosphate and many other pharmaceutical agents. Iontophoretic methods have also been employed to deliver uncharged therapeutic agents by the mechanism of induced solvent flow.

Iontophoretic devices employ two electrodes. The first electrode, called the active electrode, is the element from which the active agent is transported into the body. The second electrode, called the counter or ground electrode, serves to complete the electrical circuit through the body. In typical applications, the active electrode holds, contains or otherwise has available to it a source of the active agent. Thus, the active electrode is usually complex compared to the counter electrode.

U.S. Pat. No. 4,820,263 discloses a combination of an adhesive material and active agent for use as the active electrode. The adhesive material is a nontoxic, polymeric material that is or can be made tacky and can dissolve or disperse pharmaceutical agents.

Additional disclosure regarding iontophoresis devices can be found in our copending application Ser. No. 07/502,841 "Device and Method For Iontophoretic Drug Delivery" which is incorporated herein by reference.

Hydrogels are also known to be used for other medical purposes such as to secure other medical devices such as electrodes, bandages and the like to the human body and when so applied to provide necessary conductivity, wound protection, medicament delivery and other desirable properties for the operation of the device.

U.S. Pat. No. 4,904,247 discloses a pressure-sensitive hydrophilic laminate composite for wound dressing in which one layer of the laminate is a tacky hydrophilic polymer blend and a second layer is a non-tacky hydrophilic polymer blend. The tacky hydrophilic polymer layer is adapted for attachment to skin.

U.S. Pat. No. 4,391,278 discloses a skin electrode for sensing and stimulation utilizing a conductive adhesive mixture of a polymerized form of 2-acrylamido-2-methyl-propane sulfonic acid or one of its salts with water and/or an alcohol for attachment of the electrode to the patient's skin.

U.S. Pat. No. 4,570,629 discloses a hydrophilic biopolymer comprising a water soluble anionic protein electrolyte component derived from keratin and a water soluble cationic biopolymer poly electrolyte component selected from glucosaminoglycan and collagen for use in treating burned human skin.

However, known hydrogels have significant disadvantages in some applications due to the ionic structure of the adhesive composition. For example, iontophoresis electrodes constructed using known ionic hydrogel adhesives readily adhere to the skin but the ionic polymer and charged pharmaceutical agent tend to combine chemically into salts, thereby causing a diminished transfer of the agent through the skin.

It is therefore an object of the present invention to provide a polymeric hydrogel having a strong, amphoteric ionic structure.

It is also an object of the present invention to provide a polymeric hydrogel which would not be a source of migrating ions.

It is also an object of the present invention to provide a hydrogel matrix for delivery of drugs.

It is also an object of the present invention to provide a polymeric, amphoteric hydrogel to which desired mobile ionic species can be added in desired amounts.

It is also an object of the present invention to provide a polymeric hydrogel adhesive that can be used in diverse medical device applications including iontophoresis devices and other devices for skin contact delivery of medicaments, sensing electrodes, stimulation electrodes and wound dressings.

It is also an object of the present invention to provide a polymeric hydrogel which can be used in implantable drug delivery devices and which can be used to improve the surface characteristics of implantable medical devices.

SUMMARY OF THE INVENTION

These and other objects are achieved by the polymeric, amphoteric hydrogel of the present invention. We have discovered a polymeric, amphoteric hydrogel which can be used for medical devices which has a first polymer repeating unit having an acid group and a second polymer repeating unit having a base group such that the acid groups and base groups are present in the hydrogel with at least one such group having a strongly ionic character and with the acid groups and basic groups provided in amounts effective to provide a hydrogel with an amphoteric, nonmobile ionic structure. To provide a strongly ionic character to the hydrogel either the acid group must be a strong acid or the basic group must be a strong base. Preferably, the hydrogel combines both a strong acid group and a strong base group. Therefore, combinations of acid and base groups in the hydrogel can include a strong acid with a strong base, a strong acid with a weak base or a weak acid with a strong base. The acid groups and base groups need not be present in the hydrogel in equal numbers since it has been found that the inclusion of a relatively minor amount of repeating units containing strong base groups in a hydrogel made up of strong acid group repeating units can affect the ionic structure of the hydrogel to allow greater efficiency in the delivery of ionic drugs for iontophoresis. If desired, the ionic structure of the hydrogel can be modified to include mobile ions in desired proportions by introducing unbound anions or cations at the time the hydrogel is made. Ionic and nonionic drugs can also be included in the hydrogel. In a preferred embodiment, the acid group is provided by a strongly acidic monomer while the base group is provided by a strongly basic monomer in equimolar amounts such that the ionic structure of the hydrogel is substantially balanced.

The first polymer repeating unit contains a Lewis acid group and the second polymer repeating unit contains a Lewis base group. The acid groups in the first polymer repeating unit are preferably provided by groups including carboxylic acid, phosphoric acid or phenolic acid and most preferably by sulfonic acid. Phosphoric acid groups and sulfonic acid groups are examples of strong acid groups. The base groups in the second polymer repeating unit are preferably basic quaternary ammonium compounds and protonated amines. Groups containing basic quaternary ammonium compounds are examples of strong base groups. The polymeric hydrogel of the present invention is a synthesized material assembled from monomeric components. Monomers suitable to provide the polymer repeating units are preferably from N-substituted acrylamides. The most preferred N-substituted acrylamide monomer component for the first monomer is 2-acrylamido-2-methylpropanesulfonic acid. The most preferred N-substituted acrylamide monomer component for the second monomer is methacrylamido-propyl-trimethylammonium hydroxide.

The polymeric hydrogel can either be made with a copolymer including both first polymer repeating groups or it can be a blend of polymers which contains both polymer repeating groups.

The polymeric hydrogel can be made in aqueous solution from the monomers such as the preferred N-substituted acrylamide compounds by combining the individual acidic and basic monomers in water followed by copolymerization of the compounds. Alternatively, the polymeric hydrogel can be made by polymerizing the monomers such as the preferred acidic and basic N-substituted acrylamide monomers individually in aqueous solution and then blending the resulting polymers. Also alternatively, desired mobile ions and drugs can be introduced into the hydrogel in desired amounts by adding ionic substances and drugs which dissociate in aqueous solution.

Additives for increased tackiness, plasticity, pH control, antisepsis, antioxidation, bacterial control, syneresis, fungal control and the like can be combined with the hydrogel during polymerization or blended in with the base hydrogel polymer later depending on the desired application.

The resulting polymeric, amphoteric hydrogel can be used on a wide variety of medical devices including iontophoresis devices, medical electrodes for sensing and stimulation, wound dressings, passive drug delivery devices, medical devices implantable in the human body and the like.

For example, in an iontophoretic device, the device can include a housing that preferably is insulated, a source of current and current control preferably mounted within the housing, a counter electrode element in electrical contact with one pole of the current source and an active electrode element in electrical contact with the other pole of the current source preferably through an electrode plate.

The active electrode element can be composed of two layers. A first or adhesive layer is composed of the polymeric, amphoteric hydrogel of the present invention. A second or carrier layer contains dissolved or dispersed active pharmaceutical agent. The carrier layer is composed of a matrix that is polar and may be an organic polymer or natural or semi-synthetic material and preferably has few or no ionizable substituents. The matrix is preferably a hydratable organic polymer matrix.

The two layers of the active element can be constructed so that immediately upon their contact the active agent is released from the carrier layer to the adhesive layer. The release can occur during manufacture of the element or later by the intentional act of the user. In a preferred embodiment, the element is an insert that can be fitted onto the electrode plate within an active electrode compartment of an iontophoretic device. Alternatively, the two layer element can be permanently mounted on the electrode plate.

In yet another embodiment, a single layer device can be made from the hydrogel of the present invention to perform the functions of both carrier and adhesive.

In operation, the iontophoretic device is applied in activated form to the skin of the patient to be treated and attached to the skin by the polymeric hydrogel of the present invention. An electrical potential is then generated between the active electrode element and the skin of the patient.

DETAILED DESCRIPTION OF THE INVENTION

Figure 1:
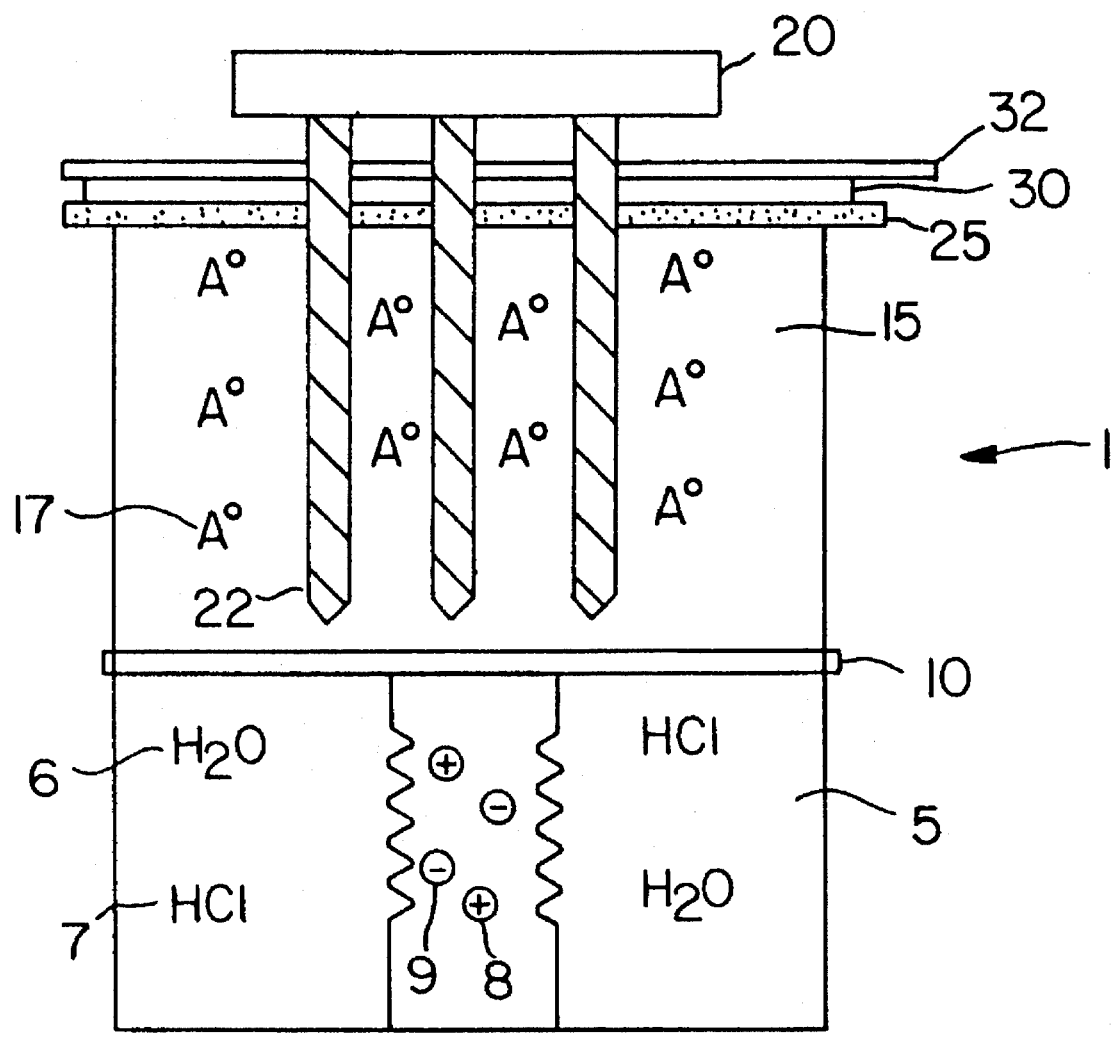
FIG. 1 is a sectional view of an iontophoresis electrode utilizing the polymeric hydrogel of the present invention.

The polymeric, amphoteric hydrogel of the present invention is intended for use on medical devices such that the medical device can be readily adhered to the patient's skin by pressing the hydrogel on the device against the skin of the patient. Alternatively, the hydrogel can be used on devices to be implanted in the human body. In skin contacting applications, the inherently tacky nature of the adhesive can provide a pressure-sensitive functional contact between the device and the skin of the patient. The hydrogel can be provided in conductive form for use on electrodes, including iontophoresis electrodes such as those described herein. The adhesive hydrogel is also capable of acting as a skincompatible barrier material in wound dressings and as a carrier for pharmaceutically active substances to be applied transdermally or to wound sites. By the term "skin" herein we mean the skin of the patient or person to be treated and it also includes the mucosa or other body surface to which a medical device may be applied. The hydrogel is also capable of acting as a cushioning or slip layer for implantable medical devices and as a matrix material for the inclusion of drugs or biocompatible surface modifiers for implantable devices.

The polymeric, amphoteric hydrogel of the present invention has a combination of substantially nonmobile acid and base groups which render the hydrogel amphoteric and moreover substantially free of migrating ions. The hydrogel has a first polymer repeating unit having an acid group and a second polymer repeating unit having a base group so that the acid groups and base groups are present in the hydrogel in amounts effective to provide the hydrogel with an amphoteric, nonmobile ionic structure. Further, at least one such group has a strongly ionic character which can provide the hydrogel with a strong ionic structure. To provide a strongly ionic character to the hydrogel, either the acid group must be a strong acid or the basic group must be a strong base. Preferably, the hydrogel combines both a strong acid group and a strong base group. Therefore, combinations of acid and base groups in the hydrogel can include a strong acid with a strong base, a strong acid with a weak base or a weak acid with a strong base. By combining both acid and base groups in the polymeric structure of the hydrogel, a zwitterion structure is formed in which the ions of the hydrogel are substantially nonmobile. The acid groups and base groups need not be present in the hydrogel in equal amounts to provide the benefits of the present invention since it has been found that the addition of a relatively minor amount of repeating units containing strong base groups to a hydrogel made up of strong acid group repeating units can significantly affect the ionic structure of the hydrogel to allow greater efficiency in the delivery of ionic drugs for iontophoresis.

An acceptable ratio of acid groups to base groups in the hydrogel will vary depending on the relative strength of the acid and base groups but generally that ratio is in the range of about 10:1 to 1:10. Preferably, the ratio is in the range of 3:1 to 1:3 and most preferably, for the most balanced ionic structure, a 1:1 ratio is employed. In a preferred embodiment, the acid group is provided by a strongly acidic monomer while the base group is provided by a strongly basic monomer and combined in substantially equimolar amounts such that the pH of the hydrogel is substantially neutral.

The ionic structure of the hydrogel can be modified to include a desired level of mobile ionic species by introducing unbound anions or cations at the time the hydrogel is formed. This can be particularly useful in iontophoresis devices which rely on certain ionic species for their operation and in medical electrodes to improve electrical conductivity. Ionic and nonionic drugs can also be included in the hydrogel matrix.

The polymeric hydrogel can either be made with the first and second polymer repeating units in a single polymeric structure. For example, the hydrogel could be a copolymer made from two different monomers in which a first monomer has a acid group while a second monomer has a base group. The adhesive could also be made with the first and second polymer repeating units in separate polymers. For example, the hydrogel could be a blend of two polymers, the first of which contains polymer repeating units having a acid group and the second of which contains polymer repeating units having a base group. The polymer or polymers which have the acid or base groups have a molecular weight of at least 5,000 to provide a substantially nonmobile ionic structure. Preferably, the molecular weight is at least about 20,000.

In a preferred embodiment, the polymeric hydrogel has a pH that is substantially neutral. Therefore, a pH in the range of about 6 to 8 is preferred in the hydrogel.

The first polymer repeating unit contains a strong Lewis acid group and the second polymer repeating unit contains a strong Lewis base group. The acidic groups in the first polymer repeating unit are preferably provided by groups including carboxylic acid, phosphoric acid or phenolic acid groups and most preferably by sulfonic acid groups. Phosphoric acid and sulfonic acid groups are examples of strong acid groups in the present invention as well as some carboxylic acid groups such as glycolic acid. The basic groups in the second polymer repeating unit are preferably basic quaternary ammonium compounds and protonated amines. Groups containing basic quaternary ammonium compounds are examples of strong base groups in the present invention. In addition to the acid groups and base groups, other acids and bases can be used to adjust the pH of the overall hydrogel composition and to provide mobile anions and cations that may be desired in the hydrogel.

The polymeric hydrogel of the present invention is a synthesized material assembled from monomeric components. Naturally occurring substances are unsuitable for use in the present invention due to the substantial impurities present therein. The polymer repeating units can be prepared from organic monomers carrying the pendant, ionizable Lewis acid and base groups. Examples include gelled and/or cross-linked water swellable polyolefins, polycarbonates, polyesters, polyamides, polyethers, polyepoxides and polyurethanes carrying such pendant substituents such as (alkyl, aryl, or aralkyl) carboxylic, phosphoric, phenolic or sulfonic acids, (alkyl, aryl or aralkyl) basic quaternary ammonium compounds and protonated amines. Preferred formulations include gel polymers of ethylenically unsaturated carboxylic or sulfonic acid such as polyacrylic acids, poly(acrylamido alkyl or aryl carboxylic or sulfonic acid), poly[N-(trimethyl aminoethyl) acrylamide] chloride and poly(acrylamido alkyl or aryl phosphoric or phenolic acid). Further detail and discussion of the hydrogel formation techniques, the gellation and cross-linking processes and modifications to develop adhesiveness and/or tackiness may be found in "Handbook of Adhesives," I. Skeist Ed., Van Nostrand Reinhold & Co., New York 1977, the disclosure of which is incorporated herein by reference.

Most preferably, the polymer repeating units are both from polymerized N-substituted acrylamide monomers. The most preferred N-substituted acrylamide polymer repeating unit component for the first polymer repeating unit is 2-acrylamido-2-methylpropanesulfonic acid (AMPS). It is preferred that the AMPS monomer be "refined" as per U.S. Pat. No. 4,650,614 "Refining of Reaction Grade 2-Acrylamido-2Methylpropane Sulfonic Acid" which is incorporated herein by reference. The most preferred N-substituted acrylamide polymer repeating unit component for the second polymer repeating unit is methacrylamido-propyl-trimethylammonium hydroxide (MAPTAH). The AMPS components and MAPTAH component can be present in the hydrogel in the mole ratio range of about 10:1 to 1:10 and preferably in the mole ratio of about 3:1 and 1:3. Additives for increased tackiness, plasticity, pH control, antisepsis, antioxidation, bacterial control, syneresis, fungal control and the like can be combined with the hydrogel during polymerization or blended in later. For example, tackifiers could include polyacrylic acid, polyvinyl pyrollidone, polystyrene sulfonic acid or its salts, karaya, xanthan, guar, or locust bean gums. Also, for example, additives for modifying the strength or cohesiveness of the hydrogel could include materials such as hydroxypropylmethylcellulose, carboxymethylcellulose, hydroxypropylguar, dextran or silica. Also, for example, humectants and plasticizers such as glycerol, propylene glycol or polyethylene glycols could be added to the hydrogel to preserve its moisture content during storage of the medical device.

The addition of other nonionic polymeric ingredients can allow the polymeric hydrogel to be adjusted to a desired ionic content. The additional polymeric ingredients may be present as a copolymer or as a blend of polymers. For example, polyvinyl alcohol (PVA), polyvinyl pyrollidone (PVP), and polymers of diacetone acrylamide, n-isopropyl acrylamide or hydroxy-ethyl-methacrylate (HEMA) could be used. Nonionic monomers such as vinyl pyrollidone or hydroxy ethyl acrylate can also be included in the structure of the hydrogel to adjust its ionic content.

The polymeric hydrogel can be made by various polymerization techniques with monomer intermolecular coupling and/or light to medium cross linking. For example, the hydrogel can be made in aqueous solution from monomers such as the preferred N-substituted acrylamide compounds by combining the individual acidic and basic compounds in water followed by copolymerization of the compounds. Alternatively, the polymeric hydrogel can be made by polymerizing the monomers such as the preferred acidic and basic N-substituted acrylamide components individually in aqueous solution and then blending the resulting polymers. In either case, the resulting amphoteric gel is hydrophilic and, as applied to medical devices, contains about 20% to 70% water. A variety of crosslinkers can be used to vary the properties of the hydrogel, for example diethylene glycol diacrylate, methylene-bis-acrylamide, triethylene glycol dimethacrylate, or tetraallyl oxyethylene. In the most preferred embodiment of the hydrogel with a balanced ionic structure of strongly ionic groups, the components are combined in essentially equimolar amounts.

If desired, the ionic structure of the hydrogel can be modified to include mobile ionic species in desired proportions by introducing unbound anions or cations at the time the hydrogel is formed. The desired mobile ions can be introduced into the hydrogel in desired amounts by adding ionic substances which dissociate in the aqueous solution described above. For example, potassium chloride can be added to improve conductivity in medical electrode applications. The added ionic substance can be a acid or base such as hydrochloric acid or sodium hydroxide which then provides a single, mobile ionic species to the hydrogel in a desired amount.

Ionic and nonionic drugs in all therapeutic areas can also be carried in the hydrogel including, but not limited to, anti-infectives (e.g. gentamicin sulfate, neomycin sulfate, or cephalosporin), analgesics, anesthetics (e.g. lidocaine hydrochloride or benzocaine), antihistamatic agents, anticonvulsants, antidepressants, antidiabetic agents, antidiarrheals, antihistamines, anti-inflammatory agents, (corticosteroids, such as hydrocortisone, betamethasone, triamcinolone acetonide, or fluocinonide), antinauseants, antispasmodics, anticholinergics, sympathomimetrics, xanthine derivatives, cardiovascular preparations, including calcium channel blockers, beta blockers, antiarrythmics, antihypertensives, diuretics, vasodilators, including general, coronary, peripheral and cerebral central nervous system stimulants, diagnostics and the like.

The resulting polymeric, amphoteric hydrogel can be used on a wide variety of medical devices including iontophoresis devices, medical electrodes for sensing and stimulation, wound dressings passive drug delivery devices, medical devices implantable in the human body and the like.

For example, in an iontophoretic device, the device can include a housing that preferably is insulated, a source of current and current control preferably mounted within the housing, a counter electrode element in electrical contact with one pole of the current source and an active electrode element in electrical contact with the other pole of the current source preferably through an electrode plate.

The active electrode element can be composed of two layers. A first or adhesive layer is composed of the polymeric, amphoteric hydrogel organic polymer of the present invention. A second or carrier layer contains dissolved or dispersed active agent. The carrier layer is composed of a matrix that is polar and may be an organic polymer or natural or semi-synthetic material and preferably has few or no ionizable substituents. The form of the matrix is preferably a hydratable organic polymer matrix. Other ingredients may be included in both layers so long as they do not adversely affect the iontophoresis process, active agent compatibility within the carrier layer and adhesive quality of the adhesive layer.

The two layers of the active element can be constructed so that immediately upon their contact the active agent is released from the carrier layer to the adhesive layer. The release can occur during manufacture of the element or later by the intentional act of the user. In a preferred embodiment, the element is an insert that can be fitted onto the electrode plate within an active electrode compartment of an iontophoretic device. Alternatively, the two layer element can be permanently mounted on the electrode plate.

In one embodiment of the active electrode element, the element can include an impermeable barrier between the two layers. The carrier layer is optionally designed to contain little or no water and to maintain about a preferred pH so that decomposition of the active agent over a long term is minimized. Breaching the impermeable barrier results in migration of the active agent from carrier layer to the adhesive layer. If the carrier layer is a solid gel, powder, hydrogel or other shape retaining material, the barrier can be a film between the two layers. If the carrier layer is fluid, semi-fluid or viscous, the barrier can be a container such as a pouch, bag or a combination of the walls of the element housing and a covering film or membrane.

A preferred embodiment of the active electrode element with impermeable barrier concerns a carrier layer solution of the active agent in neutral form. In this embodiment, the adhesive hydrogel of the present invention also contains an appropriate reagent for converting the active agent to an ionic form. Breaching the impermeable barrier during use initiates the conversion. Incorporation of higher concentrations and stability of the active agent in the active element are increased by this embodiment.

In another preferred embodiment of the active electrode element, the polymeric hydrogel of the present invention also has incorporated therein a mobile acid or base in an amount sufficient to ionize the active agent, an impermeable barrier, a carrier layer containing an active agent in neutral form but that is capable of forming a charged form by reaction with the appropriate acid or base ion, and an electrode plate of a composition that will render the counterion of the acid or base immobile.

In operation, the iontophoretic device is applied in activated form to the skin of the patient to be treated and attached to the skin by the polymeric hydrogel of the present invention. An electrical potential is then generated with an iontophoretic/electrical pulse stimulator between the active electrode element and the skin of the patient.

To construct the two layer electrode element, the adhesive layer can be formed by extrusion of the preformed hydrogel and optional other ingredients into an appropriately shaped mold or directly into the iontophoretic housing. Alternatively, the monomeric mixture can be polymerized, gelled and/or cross-linked directly within the mold or housing with addition of optional other ingredients at appropriate intervals during the polymerization. The formed adhesive layer is then allowed to cure into a shape retaining form. Those skilled in the art will readily appreciate that the methods disclosed herein for forming hydrogel in connection with an iontophoresis device can also be used to form hydrogel when making sensing electrodes, stimulation electrodes, wound dressings and other medical devices. Also, for example, the hydrogel can be coated on reinforcement materials to provide additional structure for the medical device and release-coated liners can also be used to cover the hydrogel and which can be conveniently peeled off immediately prior to use of the device.

The free-flowing mixture of carrier layer polymer and/or natural or semi-synthetic material, as well as active agent and optional other ingredients is introduced as a covering layer over the cured adhesive layer and allowed to resolidify. When the carrier layer is a liquid or semi-fluid or viscous material it is first introduced into the container and then positioned on top of the adhesive layer. In the case of a permanently mounted active electrode element, the adhesive layer is formed in situ within the iontophoretic housing by this process. Moreover, the adhesive layer may be formed before or after formation of the carrier layer within the housing. If formed before, the housing may be of two joinable parts, the first being for the adhesive layer and the second for the carrier layer. In the case of an insert, the element is formed in the mold, removed after formation and packaged for storage. When the embodiment containing the impervious barrier is constructed, the barrier is positioned onto the surface of the cured hydrogel before introducing the carrier layer with active agent or the barrier may be prepositioned so as to segregate the carrier layer with active agent from a subsequently in situ prepared hydrogel.

Referring now to FIG. 1, FIG. 1 is a sectional view of one possible embodiment of an active electrode 1 for iontophoresis which includes a layer of amphoteric hydrogel 5 according to the present invention as an adhesive layer. An impervious membrane sheet 10 is affixed between the adhesive layer 5 and a second, carrier layer 15 containing neutral active agent 17. A plunger 20 with piercing elements 22 is positioned above the membrane sheet 10 and within the carrier layer 15 so as to be capable of perforating the membrane sheet 10. The piercing elements 22 also protrude through the backing sheet 25 and the silver electrode plate 30 which is connected to the current source (not shown) through a lead 32. The backing sheet 25 may be made of cloth, paper, polymer, fiber or any other similar material. In some embodiments, it may be desirable to use a conductive material as a backing sheet as, for example, when the backing sheet is overlayed with an electrode plate 30 as shown. The hydrogel layer 5 contains water 6, and chloride ion 7. The hydrogel layer 5 also contains both positive and negative functional groups 8,9 in its polymer structure.

In operation of the active electrode 1, the plunger 20 is pushed to pierce membrane sheet 10. Water 6 in the hydrogel 5 begins to diffuse through the perforations made by piercing elements 22 and into carrier layer 15 where the dehydrated hydrogel present swells by hydration. Current from the current source (not shown) is switched on and transport of active agent begins.

The reactions involved during operation of the electrode of FIG. 1 include the following. A portion of hydrogen chloride from the amphoteric adhesive layer 5 migrates to the carrier layer 15 leaving the hydrogel layer 5 uncharged. The hydrogen cation reacts with the neutral active agent to form an ionized species available for transport. To maintain charge balance, silver at the electrode plate 30 is oxidized and reacts with the chloride to form insoluble silver chloride.

In yet another embodiment, a single layer device can be made from a hydrogel to perform the functions of both carrier and adhesive described above thereby eliminating the necessity for the barrier material. In this embodiment, the electrode uses the hydrogel of the present invention as both carrier for the drug and adhesive for attachment to the patient's skin. The drug and hydrogel can be combined and maintained in a moist state if the drug is unaffected by moist storage or, alternatively, can be combined and dried to eliminate water from the hydrogel if moisture would cause the effectiveness of the drug to diminish during storage. The electrode can then be stored in dry form and activated by reconstituting with water immediately before use.

The hydrogel of the present invention can also be used to make tape electrodes such as those used for stimulation of tissue or monitoring electrical activity in the human body as well as for grounding a patient during surgical procedures. The hydrogel may be applied and cured over a flexible backing material such as cloth or polymeric foam. Depending upon the application for the electrode, conductive materials such as metallic foil, wire mesh or conductive cloth can be used as current distributing members for the electrode in combination with the hydrogel and backing materials. The hydrogel may also have incorporated mobile ionic species such as potassium chloride which can provide conductivity required for the particular electrode application. The hydrogel may act as an adhesive to adhere the tape electrode to the skin of the patient and may be covered by a release paper which may be removed immediately before its application to the patient.

The hydrogel of the present invention can also be used to make adherent wound dressings for protecting cuts, scratches, abrasions burns, graft donor sites, ulcers of the skin and similar injuries and diseases to the skin. The hydrogel can be applied to a backing material and then covered by a release paper which may be removed immediately before application of the wound dressing to the patient. The hydrogel can also incorporate therapeutic agents such as anti-microbial agents, anti-infectives and additives such as growth factors that may be useful in treating the wound. The hydrogel can also be used in the same manner to make passive drug delivery devices in which the hydrogel is loaded with a drug which can be slowly absorbed through the skin.

The hydrogel of the present invention can also be used in implantable medical devices such as by providing a drug eluting matrix in the device. For example, a lead having an electrode tip for stimulating heart tissue or sensing electrical activity in the heart in connection with a heart pacemaker can be provided with steroid eluting capability by incorporating the desired steroid into the hydrogel of the present invention and incorporating the hydrogel into a chamber near the electrode tip.

The following examples are illustrative of the amphoteric hydrogel and medical devices of the present invention.

EXAMPLES

Example 1

Preparation of the amphoteric hydrogel of the present invention in copolymer form.

Take 5.0 grams methacrylamido-propyl-trimethylammonium hydroxide (MAPTAH) in 5.0 grams distilled water. Take 5.1 grams 2-acrylamido-2-methylpropanesulfonic acid (AMPS) in 12 grams distilled water. Mix the MAPTOAH and AMPS components together. The pH of the resulting mixture is approximately 7. Mix in 0.2 grams of 5% ammonium persulfate solution to act as the initiator. Place the resulting mixture in a 70 degree C vacuum oven, degas the system and release to a nitrogen atmosphere. Leave the material in the oven under nitrogen for 30 minutes. The result is a viscous, tacky polymer gel.

Example 2

Preparation of the polymeric hydrogel of the present invention as a blend of polymers.

Take 5.0 grams methacrylamido-propyl-trimethylammonium hydroxide (MAPTAH) in 5.0 grams distilled water. Mix in 0.1 grams of 5% ammonium persulfate solution to act as the initiator. Place the resulting mixture in a 70 degree C vacuum oven, degas the system and release to a nitrogen atmosphere. Leave the material in the oven under nitrogen for 30 minutes. Take 5.1 grams 2-acrylamido-2-methylpropane sulfonic acid (AMPS) in 12 grams distilled water. Mix in 0.1 grams of 5% ammonium persulfate solution to act as the initiator. Place the resulting mixture in a 70 degree C vacuum oven, degas the system and release to a nitrogen atmosphere. Leave the material in the oven under nitrogen for 30 minutes. Mix the polymerized MAPTAH and AMPS components together. The pH of the resulting mixture is approximately 7. The result is a viscous, tacky polymer gel.

Example 3

Use of the polymeric hydrogel of the present invention in an iontophoresis electrode.

Dissolve 0.92 grams of N', N'Methylene-bis-acrylamide in 27.5 grams deionized water. Add 40.91 grams 2-acrylamido-2-methylpropanesulfonic acid and mix until dissolved. With cooling and mixing, add 15.90 grams of a 50% by weight of a sodium hydroxide (NaOH) in water solution dropwise. Keep the temperature below 30 degrees C. 5.68 grams of an 80% solution of 2-trimethylammoniumethyl-methacrylic hydroxide (TMAEMH) is then added and mixed in. Vacuum degas the mixture for five minutes and then release the vacuum with nitrogen (keeping the sample jar covered). Add 9.09 grams of a 3% solution of 1-hydroxy-cyclohexylphenylketone in 2-propanol. Mix for an additional two minutes. Coat the solution through a mesh reinforcement layer of spun bonded polyester (Reemay 2055) onto a release coated polyester sheet material (5 mil Mylar). Cure the composition with UV radiation from a 365 nm mercury lamp for 10 minutes. After curing, a release coated polyethylene top liner is placed over the cured gel. The packaged gel sheet can then be die cut into the desired shapes for an adhesive iontophoresis electrode and used to administer anionic drug species such as Ketoprofin or salicylate.

Example 4

Use of the polymeric hydrogel of the present invention in an iontophoresis electrode.

Dissolve 0.92 grams of N', N' methylene-bis-acrylamide in 82.94 grams of a 50% in water solution of methacrylamidopropyltrimethylammonium chloride. Add 4.61 grams methacrylamidopropyl-trimethylammonium hydroxide and mix in. Mix in 2.31 grams 2-acrylamido-2-methylpropanesulfonic acid until dissolved. Add 9.22 grams of a 3% solution of 1-hydroxycyclohexylphenylketone in 2-propanol and mix in. Vacuum degas the solution. Cast a 0.020 inch thick film of this solution onto a nonwoven polyester scrim (Reemay 2055) on a release coated 5 mil Mylar film liner. Expose the monomer film to ultraviolet radiation under a nitrogen blanket for twenty minutes. The resulting hydrogel film can be used to administer Sufentanil, a cationic analgesic.

Example 5

Use of the polymeric hydrogel of the present invention in a tape electrode.

Take 50 grams methacrylamido-propyl-trimethylammonium hydroxide (MAPTAH) in 50 grams distilled water. Take 51 grams of 2-acrylamido-2-methylpropanesulfonic acid (AMPS) in 119 grams distilled water. Combine those solutions and add the following components to the mixture: 0.06 grams N'-N'methylene-bis-acrylamide, 50 grams glycerol and 7 grams of potassium chloride and 15 grams of fumed silica (Cabot M-5) and mix for 30 minutes Add 15 grams of a 3% solution of [1-hydroxy cyclohexyl phenyl ketone] in 2-propanol Mix for an additional 5 minutes. Vacuum degas the mixture for 10 minutes. Coat the solution through a mesh reinforcement layer of spun bonded polyester (Reemay 2055) onto a release coated polyester sheet material (5 mil Mylar). Then cure the composition with UV radiation from a 365 nm mercury lamp for 20 minutes. After curing, place a release coated polyethylene liner over the cured gel. The packaged gel sheet can then be die cut into the desired shapes and converted into biomedical electrodes.

Example 6

Use of the polymeric hydrogel of the present invention in a wound dressing.

Take 50 grams methyacrylamido-propyl-trimethylammonium hydroxide (MAPTAH) in 50 grams distilled water. Take 51 grams of 2-acrylamido-2-methylpropanesulfonic acid (AMPS) in 119 grams distilled water. Mix the MAPTAH and AMPS compositions together. Add the following components to the mixing solution: 0.08 grams N'-N' methylene-bis-acrylamide, 50 grams propylene glycol 600 and 15 grams fumed silica (Cabot M-5) and mix for 30 minutes Add 15 grams of a 3% solution of [1-hydroxy cyclohexyl phenyl ketone] in 2-propanol. Mix for an additional 5 minutes. Vacuum degas the mixture for 10 minutes. Coat the solution through a mesh reinforcement layer of spun bonded polyester (Reemay 2055) onto a release coated polyester sheet material (5 mil Mylar) to a thickness of 0.025 nominal. Then cure the composition with UV radiation from a 325 nm mercury lamp for 20 minutes. After curing, the gel can be covered with a polyurethane backing and cut into the desired shapes.

Example 7

Preparation of the polymeric hydrogel of the present invention in copolymer form using acrylic acid as a component.

Prepare a polymeric hydrogel substantially as described in Example 1 but substitute 1.77 grams of acrylic acid for the AMPS component.

Example 8

Preparation of the polymeric hydrogel of the present invention in copolymer form using 2-trimethylammoniumethyl-methacrylic hydroxide (TMAEMH) as a component.

Prepare a polymeric hydrogel substantially as described in Example 1 but substitute 4.66 grams of 2-trimethylammoniumethylmethacrylic hydroxide (TMAEMH) for the MAPTAH component.

Example 9

Preparation of the polymeric hydrogel of the present invention in copolymer form using methacrylic acid as a component.

Prepare the polymeric hydrogel substantially as described in Example 1 but substitute 2.11 grams of methacrylic acid for the AMPS component.

Example 10

Preparation of the polymeric hydrogel of the present invention in copolymer form using N' N-dimethylaminoethylmethacrylate (DMAEMA) as a component.

Prepare the polymeric hydrogel substantially as described in Example 1 but substitute 3.87 grams of N' N-dimethylaminoethylmethacrylate (DMAEMA) for the MAPTAH component.

While the invention has been described above in connection with the particular embodiments and examples, one skilled in the art will appreciate that the invention is not necessarily so limited and that numerous other embodiments, examples, uses and modifications of and departures from the embodiments, examples and uses may be made without departing from the inventive concepts.

We claim:

1. An amphoteric, hydrophilic hydrogel adhesive for adhering medical devices to human skin comprising a copolymer having:

first polymer repeating units having a pendant strong acid group selected from the group consisting of carboxylic acid, phosphoric acid, phenolic acid or sulfonic acid; and second polymer repeating units having a pendant strong base group selected from the group consisting of quaternary ammonium salts and protonated amines, at least one of said first and second polymer repeating units being an N-substituted acrylamide.

2. The hydrogel of claim 1 wherein the mole ratio of first polymeric repeating units to second polymeric repeating units is in the range of about 10:1 to about 1:10.

3. The hydrogel of claim 1 wherein the hydrogel includes as its first polymeric repeating unit an N-substituted acrylamide.

4. The hydrogel of claim 3 wherein the N-substituted acrylamide is 2-acrylamido-2-methylpropanesulfonic acid.

5. An amphoteric, hydrophilic hydrogel for adhering medical devices to human skin comprising:

a copolymer having as a first polymer repeating unit component an N-substituted acrylamide having a pendant sulfonic acid group and as a second polymer repeating unit component an N-substituted acrylamide having a pendant base group.

6. The hydrogel of claim 5 wherein the N-substituted acrylamide is 2-acrylamido-2-methylpropanesulfonic acid.

7. The hydrogel of claim 5 wherein the second polymer repeating unit is methacrylamido-propyl-trimethylammonium hydroxide.

8. The hydrogel of claim 5 wherein the mole ratio of the first polymer repeating unit component to the second polymer repeating unit component is in the range of about 10:1 to 1:10.

9. A medical device having an amphoteric hydrogel component according to claim 1 or 8.

10. The medical device of claim 9 wherein the medical device is a medical electrode.

11. The medical device of claim 10 wherein the medical electrode is an iontophoresis electrode.

12. The medical device of claim 10 wherein the medical electrode is a sensing electrode.

13. The medical device of claim 10 wherein the medical electrode is a stimulation electrode.

14. The medical device of claim 9 wherein the medical device is a wound dressing.

15. The medical device of claim 9 wherein the medical device is a passive drug delivery device.

16. The medical device of claim 9 wherein the hydrogel also comprises a drug.

17. A method for making a medical device having an amphoteric, hydrophilic hydrogel for attachment to human skin comprising the steps of:

a. dissolving a first monomeric constituent having an acid group in water;

b. dissolving a second monomeric constituent having a base group in water, at least one of said first and second monomeric constituents being an N-substituted acrylamide and at least one of said acid group and said base group having a strongly ionic character, c. combining the first and second dissolved monomeric constituents;

d. copolymerizing the combined first and second monomeric constituents; and e. applying the copolymer to a medical device.

18. The method of claim 17 wherein the first monomeric constituent is 2-acrylamido-2-methylpropanesulfonic acid.

19. The method of claim 17 also comprising the steps of:

adding an ultraviolet catalyst in combination with the first and second monomeric constituents; and applying ultraviolet light.

20. The method of claim 17 wherein a crosslinking agent is included with the monomeric constituents.

21. The amphoteric hydrogel of claim 1 or 8 also comprising a drug.

* * * * *